United States Patent [19]

Karges et al.

[11] 4,033,824
[45] July 5, 1977

[54] PROCESS FOR THE DETERMINATION OF PLASMINOGEN

[75] Inventors: Hermann Erich Karges; Norbert Heimburger, both of Marburg-Marbach; Eckart Jacobi, Erkrath, all of Germany

[73] Assignee: Behringwerke Aktiengesellschaft, Marburg an der Lahn, Germany

[22] Filed: July 24, 1975

[21] Appl. No.: 598,626

[30] Foreign Application Priority Data

July 26, 1974 Germany .................... 2435988

[52] U.S. Cl. ........................... 195/99; 195/103.5 R
[51] Int. Cl.² ................... G01N 33/00; G01N 31/14
[58] Field of Search ................ 195/103.5 R, 99

[56] References Cited

UNITED STATES PATENTS 3,778,352  12/1973  Bishop et al. ............... 195/103.5 R
3,853,710  12/1974  Innerfield .................... 195/103.5 R

OTHER PUBLICATIONS

Flute, "The Assessment of Fibrinolytic Activity in the Blood," Brit. Med. Bull., vol. 20, No. 3 (1964).
Christensen, "Methods for Measuring the Activity of Components of the Streptococcal Fibrinolytic System, and Streptococcal Desoxyribonuclease," J. Clin. Invest. 28, (1949), pp. 163–172.

*Primary Examiner*—Lionel M. Shapiro
*Assistant Examiner*—C. A. Fan
*Attorney, Agent, or Firm*—Curtis, Morris & Safford

[57] ABSTRACT

The invention relates to a process for the analytical determination of human plasminogen which comprises mixing a liquid containing diluted human plasminogen with
  a. a catalyst, such as streptokinase, converting human plasminogen into human plasminogen activator,
  b. fibrinogen and
  c. a plasminogen, such as the plasminogen of a ruminant, e.g. bovine plasminogen, which cannot be activated by the catalyst and
  d. thrombin
and determining the coagulation of the mixture.

7 Claims, No Drawings

PROCESS FOR THE DETERMINATION OF PLASMINOGEN

The invention relates to a process for the analytical determination of human plasminogen by measuring the coagulation time in a sample.

The invention especially refers to the determination of plasminogen in human blood and body liquids. The knowledge of the content of plasminogen is especially important in the case of patients undergoing fibrinolytic or anti-fibrinolytic therapy, furthermore in the case of patients suffering from thromboembolia or a global disturbance of coagulation.

To determine the content of plasminogen of a plasma or serum sample a series of methods are available which are based on different principles, have a different sensitivity or are more or less liable to troubles and are more or less time-consuming for the determination. The difference between the biological tests consists, in principle, in that either the plasminogen of the sample is converted into plasmin and is determined for example in the fibrin plate technique according to Astrup or the plasminogen is converted into a plasminogen activator with the aid of a catalyst, for example streptokinase, and is determined as the activator. Such determination for example can be carried out by the Clot-Lysis method according to Christensen in which the activator formed may be measured via the formation of plasmin.

In an earlier Patent Application a process for measuring the content of plasminogen has been proposed, in which the formation of fibrin in a test plasma free of antiplasmin is retarded after activation of the plasminogen with addition of thrombin and the plasminogen content is found by the determination of the delay of the coagulation time. A considerable drawback of this process, however, is that the activity of the antiplasmin of the plasma of the patient has to be eliminated with isoamyl alcohol. That is why its use for the routine determination of plasminogen in clinical laboratories implies relatively high expenditures and is not faster than, for example, the Clot-Lysis method.

Therefore it was desired to improve the suggested process.

It has now been found that the determination of plasminogen can be considerably simplified when the plasminogen in a sample, for example in diluted plasma or serum, is converted with the aid of a catalyst into a plasminogen activator and the amount of the activator is determined in a test system containing an excess of a plasminogen, which is not activated by the catalyst. The coagulation time of the test batch with thrombin is fixed as measuring standard for the unknown plasminogen content.

Therefore, the invention relates to a process for the determination of plasminogen in human body liquids by measuring the coagulation time of a fibrinogen-containing solution, which consists in mixing with one another a. a diluted body liquid containing human plasminogen,
b. a catalyst converting human plasminogen into human plasminogen activator,
c. fibrinogen,
d. a plasminogen which cannot be activated by the catalyst and finally
e. thrombin, determining the coagulation time of the batch and correlating the coagulation time with the amount of plasminogen.

The process is particularly suitable for determining plasminogen in the plasma, serum or in other body liquids of human subjects.

The process is based on the consideration that human plasminogen is capable of forming a complex with some biological catalysts, for example the metabolism product of $\beta$-hemolysing streptococci, streptokinase, which complex has an enzymatic activity comparable with endogenic activators of plasminogen. On the other hand, plasminogen from animals, especially from ruminants, for example bovine plasminogen, is not activated by streptokinase. The complex of human plasminogen and streptokinase catalyses the conversion of human and animal plasminogen into plasmin.

From this point of view the essential point of the present process is that on one hand a catalyst, for example streptokinase, is used which is capable of converting human plasminogen into a human plasminogen activator. On the other hand this catalyst converts an added plasminogen, which, phylogenetically, is not related to the human plasminogen, into plasmin, not directly in most of the cases, but only via an activated intermediate stage. It is known that plasmin represents a very active proteinase capable of decomposing fibrinogen for example. In a coagulation batch the coagulation time is the more retarded the stronger the fibrinogen has been degraded by plasmin present.

According to the previous statements, any other catalytically active substance which is capable of converting the total amount of plasminogen present into an activator may be used instead of streptokinase.

Therefore it could be shown by the present process that a relation between the amount of plasminogen present and the coagulation time measured in a coagulation batch can be established. It has proved suitable to dilute the body liquids to be tested 1:5 to 1:5000 with an aqueous medium, preferably with an isotonic salt solution, which may be buffered. The amount of the catalyst should be in excess with regard to the amount of plasminogen. When using streptokinase as a catalyst this means a molar ratio of streptokinase: plasminogen >1:1. Within normal measuring ranges it is sufficient to add per ml of the diluted body liquid 250 – 5000 units of streptokinase (according to Christensen) or a corresponding equivalent of another catalytically active substance which is capable of converting the total amount of plasminogen into activator. According to Christensen, J. Clin. Invest. 28, 163–172 (1949), one unit of streptokinase is that amount of streptokinase required to lyse, in 10 minutes, the clot formed by incubating at 35° C a mixture of 0.1 ml of the streptokinase diluted in gelatin buffer, 0.4 ml of bovine fibrinogen (0.25% in borate buffer), 0.5 mg. of Harvard Fraction III (0.25 in borate buffer) as a plasminogen source, and 0.1 ml of hemostatic globulin, diluted 1:3 in borate buffer.

Furthermore the batch shall expediently contain per ml 1 to 20 mg of fibrinogen, an amount of 1 to 80 units of plasminogen which cannot be activated by the catalyst (one unit of plasminogen corresponds to a content of plasminogen of one ml of normal bovin plasma) and finally 0.1 – 1.0 units of thrombin. It is evident to the expert that a higher amount of fibrinogen requires a smaller amount of thrombin for coagulation in the same unit of time or that the coagulation time of the amount of fibrinogen is in inverse proportion. The coagulation time, which according to the process of the invention is correlated to the amount of plasminogen, may expediently be determined with the aid of measuring devices, the so-called coagulometers, for example in a ball coagulometer.

Furthermore, changes in the buffer medium may lead to changes in the coagulation times. Thus, a stronger alkaline buffer yields prolonged coagulation times in an otherwise unchanged test batch. But such modifications do not influence the final result of the determination of the plasminogen content, since the plasminogen content of the sample is read off from a calibrated curve which is drawn accordingly in each case.

It has proved advantageous to proceed in practice as follows: To a diluted body liquid containing human plasminogen a catalyst is added which converts human plasminogen into human plasminogen activator; the mixture is added to a solution containing fibrinogen and a plasminogen which cannot be activated by the catalyst; the batch is finally brought to coagulation with thrombin, and the coagulation time is determined and correlated to the amount of plasminogen. Alternatively a body liquid containing human plasminogen is added to a mixture of a. a catalyst converting human plasminogen into human plasminogen activator,
b. fibrinogen and
c. a plasminogen which cannot be activated by the catalyst; the batch is finally brought to coagulation with thrombin, and the coagulation time is determined and correlated with the amount of plasminogen.

An especially advantageous reagent for the determination of plasminogen contains, for example, a mixture of bovine fibrinogen containing bovine plasminogen with streptokinase. The composition of the mixture is preferably between 2 and 8 mg of bovin fibrinogen containing bovin plasminogen and 250 to 5000 units of streptokinase in a solid form or dissolved in 1 ml of the suitable buffer solution.

In the clinical laboratory, reaction batches are preferred with the aid of which the methods of determination may be simplified. A reactant for the determination of plasminogen could have, for example, the following composition, whereby special requirements could give rise to fractional or multiple amounts of the indicated amount of the corresponding substances.

| Reactant | | |
|---|---|---|
| 1. Bovine fibrinogen | 60 mg | |
| 2. Steptokinase | 75,000 I.U. (according to Christensen) | |
| 3. Thrombin | 60 NIH-units (national Inst. of Health (NIH)) | |
| This test batch may be completed, if desired, by. | | |
| 4. slightly alkaline buffer solution, for example diethyl barbiturate-Na-acetate-HCl pH 7.6 | | 0.06 M |
| 5 Standard human plasma | about | 1 ml |

If desired, the components 1 and 2 may be jointly dissolved and lyophilized and in this form used in a test equipment as a single component.

With the aid of the suggested test equipment it is possible to draw the calibrated curve for the relation of the amount of plasminogen and the coagulation time and for the determination of the plasminogen of 25 unknown solutions containing human plasminogen. This is contained in the following test description:

DRAWING OF THE CALIBRATION CURVE

A glass ball ($\phi$ 2 mm) was introduced into each of 10 test tubes of polystyrene 14.5 × 84 mm. in five of the little tubes the coagulation time of the standard plasma should be carried out without activation by streptokinase. In the remaining five tubes the coagulation time is determined after activation with streptokinase. The coagulation times were measured in five different dilutions whereby, in each case, a control is effected without plasma dilution. The plasma is previously diluted 1:20 with 0.06 M of diethyl-barbiturate-Na-acetate-HCl and the further dilution with the same solution was carried out in the way that the tubes to be tested contained 100%, 50%, 25%, 12.5% and 0% of the plasma dilution. In the samples activated with streptokinase, 0.1 ml of a streptokinase solution of 20,000 I.U. per ml were added per 2 ml of a plasma predilution, and the whole was allowed to stand for 30 seconds at room temperature.

The following solutions were required for the coagulation batches described below:
1. Bovine fibrinogen solution with 4 mg/ml of bovine fibrinogen
2. Thrombin solution with 2 NIH units/ml of thrombin.

The coagulation times indicated result from the following test batch. The average values of the coagulation times obtained in a double determination are plotted on two superposed logarithm papers; the curve may be used as calibration curve for the further determinations.

| Test batch |
|---|
| 0.4 ml of bovine fibrinogen solution |
| + 0.2 ml of plasma dilutions, activated or not |
| 2 minutes incubation (37° C) |
| + 0.1 ml of thrombin |

According to the plasma dilution used, such batch provided the following coagulation times in seconds:

| Plasma not activated | | | |
|---|---|---|---|
| 100% | - 26.3 / 26.3 | = | 26.3" |
| 50% | - 24.6 / 25.1 | = | 24.9" |
| 25% | - 24.3 / 24.0 | = | 24.2" |
| 12.5% | - 23.4 / 23.2 | = | 23.3" |
| 0% | - 23.2 / 23.1 | = | 23.2" |
| Plasma activated | | | |
| 100% | - 40.5 / 39.0 | = | 39.8" |
| 50% | - 34.8 / 34.0 | = | 34.4" |
| 25% | - 29.5 / 29.3 | = | 29.4" |
| 12.5% | - 26.6 / 26.5 | = | 26.6" |
| 0% | - 23.1 / 23.2 | = | 23.2" |

TESTING OF UNKNOWN SERA OR PLASMAS

The serum or plasma samples to be tested were prediluted 1:20 like the standard human plasma dilution, were mixed with 0.1 ml of streptokinase (20,000 units/ml), and maintained for 30 seconds at room temperature. Then the incubated sample, diluted 1 + 1, was used in the test batch to determine the coagulation time. From the resulting coagulation time of 37 seconds and with the aid of the calibrated curve and the assumption that standard human plasma contains 5000 U/ml of plasminogen, it is possible to calculate the amount of plasminogen in the tested sample, for example with 70% of this value corresponding to 3500 units of plasminogen/ml. With regard to the dilution of 1:2 effected above, the content of plasminogen of the sample was 7,000 U/ml.

The same results were obtained if the pre-diluted body liquid containing human plasminogen was added to a mixture of plasminogen-containing bovine fibrinogen with 500 U/ml of streptokinase, the batch was incubated for 2 minutes at 37° C and then brought to coagulation with the thrombin solution indicated.

If it appeared, for example, that a body liquid to be tested would yield in the test system a high content of plasminogen which cannot be determined, the sample was expediently prediluted accordingly and this dilution was taken into account in the determination.

In case of a too low content of plasminogen one should proceed in a corresponding way.

What we claim is:

1. A method for the analytical determination of human plasminogen, which comprises mixing a liquid containing diluted human plasminogen with
   a. streptokinase,
   b. fibrinogen,
   c. the plasminogen of a ruminant, and
   d. thrombin,
and then determining the coagulation time of the mixture.

2. A method as in claim 1 wherein streptokinase is added to a diluted body liquid containing human plasminogen, the mixture is added to a solution containing fibrinogen and the plasminogen of a ruminant, this second mixture is brought to coagulation with thrombin, and the coagulation time is determined.

3. A method as in claim 1 wherein a diluted body liquid containing human plasminogen is added to a mixture of
   a. streptokinase,
   b. fibrinogen, and
   c. the plasminogen of a ruminant,
the resultant mixture is brought to coagulation with thrombin, and the coagulation time is determined.

4. A method as in calim 1 wherein 250 to 5,000 units of streptokinase, as defined by Christensen, are mixed, per milliliter of an aqueous solution of a body fluid prediluted 1:5 to 1:1500.

5. A method as in claim 1 wherein said plasminogen of a ruminant is bovine plasminogen.

6. A reagent for the determination of human plasminogen, said reagent consisting essentially of
   a. streptokinase,
   b. fibrinogen,
   c. the plasminogen of a ruminant, and
   d. thrombin.

7. A reagent as in claim 6 wherein said fibrinogen is bovine fibrinogen and said plasminogen of a ruminant is bovine plasminogen.